United States Patent
Hayward et al.

(10) Patent No.: US 6,537,952 B2
(45) Date of Patent: Mar. 25, 2003

(54) FOAMING ANTI-BACTERIAL CLEANSING SKIN PRODUCT WITH LOW WATER INSOLUBLE EMOLLIENTS AND FOAM DISPENSER

(75) Inventors: Christine Hayward, Torrington, CT (US); Rosa Paredes, Shelton, CT (US)

(73) Assignee: Unilever Home and Personal Care, USA division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/908,381

(22) Filed: Jul. 18, 2001

(65) Prior Publication Data

US 2002/0045554 A1 Apr. 18, 2002

Related U.S. Application Data

(60) Provisional application No. 60/229,202, filed on Aug. 31, 2000.

(51) Int. Cl.$^7$ ................................................. A61K 7/50
(52) U.S. Cl. ..................... 510/130; 510/136; 510/424; 510/428; 510/480; 510/504
(58) Field of Search ................................ 510/130, 136, 510/424, 428, 480, 504

(56) References Cited

U.S. PATENT DOCUMENTS

| | | |
|---|---|---|
| 3,962,150 A | 6/1976 | Viola |
| 5,635,469 A | 6/1997 | Fowler et al. |
| 6,030,931 A | 2/2000 | Vinski et al. |

FOREIGN PATENT DOCUMENTS

| | | |
|---|---|---|
| WO | 9117237 | 11/1991 |
| WO | 9915133 | 1/1999 |
| WO | 9939689 | 12/1999 |
| WO | 00/66079 | 9/2000 |

*Primary Examiner*—Necholus Ogden
(74) *Attorney, Agent, or Firm*—Alan A. Bornstein

(57) ABSTRACT

A foaming cleansing product is provided as a cleansing composition packaged in a non-aerosol pump dispenser. The dispenser includes a container for holding a liquid composition, a dispensing head with a housing enclosing a pump mechanism and a screen material in the flow path to convert liquid composition into a foam. The cleansing composition comprises an anionic surfactant, and at least one surfactant selected from a nonionic and an amphoteric surfactant, a cationic polymer, and a hydrophobic antibacterial agent, and contains less than 0.05 wt. % of a water insoluble emollient; said composition being dispensed by the pump dispenser to provide a foam. The total amount of surfactants in the inventive composition does not exceed 12 wt. %, and preferably does not exceed 10.5 wt. %.

15 Claims, No Drawings

FOAMING ANTI-BACTERIAL CLEANSING SKIN PRODUCT WITH LOW WATER INSOLUBLE EMOLLIENTS AND FOAM DISPENSER

This application claims the benefit of U.S. provisional application No. 60/229,202, filed Aug. 31, 2000.

SUMMARY

The instant invention is a foaming cleansing product that provides a more sanitary washing experience within a preferred embodiment a countertop dispenser, and an instant foam, and superior deposition of anti-bacterial agent.

Preferably the inventive product is used with a countertop mechanical pump allowing the foam to be dispensed directly onto the hands without soiled hands touching (and soiling) the pump or the sink faucet. Preferably the pump is situated in a stable position so that the forearm can be used to depress the pump and dispense the product. This results in a more hygienic cleansing process. In addition, initial dilution with water is not required since the foam can be distributed prior to rinsing.

An unexpected benefit of the inventive foamed cleansing product is improved delivery of an anti-bacterial agent, when present, from an instant foam delivery. This form of application unexpectedly enhances the delivery of antibacterial agent, since the same amount of agent is applied directly to the skin in the form of concentrated foam or lather as compared to dilution required by standard hand cleansing liquids to make lather for even distribution of the product on the skin.

A further unexpected benefit of the inventive cleansing product is the enhanced deposition of the hydrophobic anti-bacterial agent on the skin, such as triclosan, compared to the deposition of the same agent in the liquid cleansing product with without the foam.

A still further unexpected benefit of the inventive cleansing product is the substantially improved cleansing performance with waxy type makeup, and the like, compared to the use of the liquid cleansing product without the foam.

DETAILED DESCRIPTION

In one aspect, the inventive composition comprises a surfactant blend including an anionic surfactant, and at least one surfactant selected from a nonionic and an amphoteric surfactant, a cationic polymer, and a hydrophobic antibacterial agent, and contains less than 0.05 wt. % of a water insoluble emollient; said composition being dispensed by a mechanical pump to provide a foam, i.e. a mixture of air and liquid. Preferably the foam has a density range of 0.05 to 0.20 g/mll Preferably the inventive cleansing product has a weight ratio of anionic surfactants to the sum of nonionic and amphoteric surfactants in the range of 0.2 to 1 to 3 to 1; more preferably in the range of 1.5 to 1 to 2.5 to 1.

As used herein, the term hydrophobic in relation to anti-bacterial component means a material which is more lipid soluble, i.e. non-aqueous soluble, than aqueous soluble. The total amount of surfactants in the inventive composition does not exceed about 12.0 wt. %, and preferably does not exceed 10.5 wt. %. The viscosity of the inventive composition is in the range of 1 to 500 cps, preferably 1 to 200 cps at 25 C as measured by a Brookfield HBDVII+viscometer using 0.5 rpm and spindle #41. Preferably the composition contains a water-soluble emollient, including one or more polyhydric alcohols, more preferably glycerin and polyethylene glycol. Preferably the water-soluble emollient is in the concentration range of about 0.5 to 10 wt. %.

Water insoluble emollients require sufficient solubilizers such as surfactants when formulated into aqueous systems. With regard to the inventive composition, the pump requires a low surfactant concentration for optimum viscosity and foam production which limits the total amount of water insoluble material (including fragrance and the hydrophobic anti-bacterial agent) to a level capable of being dispersed or suspended therein. Furthermore, the inventive composition provides for excellent skin feel as determined by art recognized techniques, notwithstanding the lack of water insoluble emollients.

Compositions of the present invention preferably are free of any oil phase, especially free of water insoluble emollients. The term "free" means less than 0.05%, preferably less than 0.01% emollient, and water insoluble means any emollient having a solubility in distilled water at 25 C of less than about 1 gm per 100 mL, more preferably less than about 0.1 gm per 100 mL. Absent water insoluble emollients, the compositions can be transparent and have improved foamability.

In another aspect of the invention, enhanced deposition of hydrophobic anti-bacterial agents to the skin is provided which accompanies the application of the inventive composition. This effect is illustrated in Example 2 below.

In a further aspect of the invention, surprisingly efficient waxy cosmetics removal is provided following the application and rinsing of the inventive composition. Waxy cosmetics are here defined as cosmetics containing wax such as beeswax, carnauba wax, paraffin wax, and the like, preferably at a level in excess of about 10 wt. %. Representative examples include mascara, lipstick, cream blush, and the like. Such cosmetics may also optionally contain film forming polymers such as polyvinylpyrrolidone and copolymers of vinylpyrrolidone with e.g. polyurethane; and the like. This effect is illustrated in Example 3 below.

Anionic Surfactants

A further component of cleansing compositions according to the present invention is that of an anionic surfactant. Illustrative but not limiting examples include the following classes:

(1) Alkyl benzene sulfonates in which the alkyl group contains from 9 to 15 carbon atoms, preferably 11 to 14 carbon atoms in straight chain or branched chain configuration. Especially preferred is a linear alkyl benzene sulfonate containing about 12 carbon atoms in the alkyl chain.

(2) Alkyl sulfates obtained by sulfating an alcohol having 8 to 22 carbon atoms, preferably 12 to 16 carbon atoms. The alkyl sulfates have the formula ROSO3—M+where R is the C8-22 alkyl group and M is a mono- and/or divalent cation.

(3) Paraffin sulfonates having 8 to 22 carbon atoms, preferably 12 to 16 carbon atoms, in the alkyl moiety. These surfactants are commercially available as Hostapur SAS from Hoechst Celanese.

(4) Olefin sulfonates having 8 to 22 carbon atoms, preferably 12 to 16 carbon atoms. Most preferred is sodium C14–C16 olefin sulfonate, available as Bioterge AS 40.®.

(5) Alkyl ether sulfates derived from an alcohol having 8 to 22 carbon atoms, preferably 12 to 16 carbon atoms, ethoxylated with less than 30, preferably less than 12, moles of ethylene oxide. Most preferred is sodium lauryl ether sulfate formed from 2 moles average ethoxylation, commercially available as STEOL CS230 or Standopol ES-2.(R).

(6) Alkyl glyceryl ether sulfonates having 8 to 22 carbon atoms, preferably 12 to 16 carbon atoms, in the alkyl moiety.

(7) Fatty acid ester sulfonates of the formula: R1 CH(SO3—M+)CO2 R2 where R1 is straight or branched alkyl from about C8 to C18, preferably C12 to C16, and R2 is straight or branched alkyl from about C1 to C6, preferably primarily C1, and M+represents a mono- or divalent cation.

(8) Secondary alcohol sulfates having 6 to 18, preferably 8 to 16 carbon atoms.

(9) Fatty acyl isethionates having from 10 to 22 carbon atoms, with sodium cocoyl isethionate being preferred.

(10) Dialkyl sulfosuccinates wherein the alkyl groups range from 3 to 20 carbon atoms each.

(11) Alkanoyl sarcosinates corresponding to the formula RCON(CH3)CH2 CH2 CO2 M wherein R is alkyl or alkenyl of about 10 to about 20 carbon atoms and M is a water-soluble cation such as ammonium, sodium, potassium and trialkanolammonium. Most preferred is sodium lauroyl sarcosinate.

Nonionic Surfactants:

Co-surfactants are present in the inventive composition to aid in the foaming, detergency and mildness properties. At least one surfactant selected from a nonionic and amphoteric surfactants are the preferred co-surfactants. Suitable nonionic surfactants include C10–C20 fatty alcohol or acid hydrophobes condensed with from 2 to 100 moles of ethylene oxide or propylene oxide per mole of hydrophobe; C2–C10 alkyl phenols condensed with from 2 to 20 moles of alkylene oxides; mono- and di-fatty acid esters of ethylene glycol such as ethylene glycol distearate; fatty acid monoglycerides; sorbitan mono- and di-C8–C20 fatty acids; and polyoxyethylene sorbitan available as Polysorbate 80 and Tween 80.(R). as well as combinations of any of the above surfactants.

Exemplary non-ionic surfactants suitable for use in the compositions according to the present invention include primary amines such as cocamine (available as Adagen 160D ® from Witco) and, in a preferred embodiment, alkanolamides such as cocamide MEA (available as Empilian CME ® from Albright and Wilson), lauramide MEA (available as Empilan LME ® from Albright and Wilson), lauramide MIPA, lauramide DEA, and mixtures thereof, and the like.

Other useful nonionic surfactants include alkyl polyglycosides, saccharide fatty amides (e.g. methyl gluconamides) as well as long chain tertiary amine oxides. Examples of the lafter category are: dimethyldodecylamine oxide, oleyldi(2-hydroxyethyl)amine oxide, dimethylocty-lamine oxide, dimethyldecylamine oxide, dimethyltetrade-cylamine oxide, di(2-hydroxyethyl)tetradecylamine oxide, 3-didodecoxy-2-hydroxypropyldi(3-hydroxypropyl)amine oxide, and dimethylhexadecylamine oxide.

Amounts of the nonionic surfactant may range from 0.5 to 5 Wt. %, preferably from 1 to 4 wt. %, and most preferably from 2 to 3 wt. %.

Amphoteric Surfactants

Amphoteric surfactants such as betaines may be used in the inventive formula. Suitable betaines may have the general formula RN+(R1)2 R2 COO— wherein R is a hydrophobic moiety selected from the group consisting of alkyl groups containing from 10 to 22 carbon atoms, preferably from 12 to 18 carbon atoms; alkyl aryl and aryl alkyl groups containing 10 to 22 carbon atoms with a benzene ring being treated as equivalent to about 2 carbon atoms, and similar structures interrupted by amido or ether linkages; each R1 is an alkyl group containing from 1 to 3 carbon atoms; and R2 is an alkylene group containing from 1 to about 6 carbon atoms. Sulfobetaines such as cocoamidopropyl sultaine are also suitable.

Examples of preferred betaines are dodecyl dimethyl betaine, cetyl dimethyl betaine, dodecyl amidopropyldim-ethyl betaine, tetradecyldimethyl betaine, tetradecylami-dopropyldimethyl betaine, and dodecyidimethylammonium hexanoate. Most preferred is cocoamidopropyl betaine available as Tegobetaine F.(R). sold by Th. Goldschmidt AG of Germany. Amounts of the betaine may range from about 0.5 to 5%, preferably from about 1 to 4%, more preferably from 2 to 3% by weight of the total composition.

Specific examples of these amphoteric surfactants include the alkali, alkaline earth, ammonium and trialkanolammo-nium salts of cocoamphoacetate, cocoamphodiacetate, cocoamphopropionate, cocoamphodipropionate and mixtures thereof. Most preferred is sodium cocoamphoacetate available as Miranol HMA from the Rhone Poulenc Corporation. Similar surfactants are also available as Amphoterge. (R). from Lonza Inc., Fair Lawn, N.J. While the sodium salt is preferred, other cations can also be employed including lithium, potassium, magnesium and calcium. Amounts of the amphoteric surfactant may range from about 0 to 12%, preferably from about 1 to 10.5%, more preferably from about 2 to 6% by weight.

Moisturizing Ingredients

Moisturizing ingredients may also be included in compositions of the present invention. Water soluble moisturizers or emollients such as polyhydric alcohol-type humectants are particularly preferred. Typical polyhydric alcohols include glycerol (also known as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof, and the like. For best results at least one humectant is preferably glycerin. The amount of humectant may range anywhere from about 0.5 to 10.0%, preferably between 1 and 2% by weight of the composition.

Preservatives

Preservatives can desirably be incorporated into the cosmetic compositions of this invention to protect against the growth of potentially harmful microorganisms. Suitable preservatives are DMDM Hydantoin, and EDTA salts. Other useful preservatives include alkyl esters of para-hydroxybenzoic acid, propionate salts, and quaternary ammonium compounds, iodopropynyl butyl carbamate, phenoxyethanol, methyl paraben, propyl paraben, imidazo-lidinyl urea, sodium dehydroacetate and benzyl alcohol, and the like. The preservatives should be selected having regard for the use of the composition and possible incompatibilities between the preservatives and other ingredients in the composition. Preservatives are preferably employed in amounts ranging from 0.01% to 2% by weight of the composition.

Minor adjunct ingredients may be present in the cosmetic compositions. Among them may be the water-soluble vitamins, colorants, fragrances and opacifiers, and the like. Each of these substances may range from 0.05 to 5%, preferably between 0.1 and 3% by weight.

Advantageously, the compositions of the invention may contain a foam densifying agent. Examples of this substance are waxy materials with a melting point greater than 20.degree. C., preferably greater than 40.degree. C. Illustrative are ethoxylated glyceride esters such as PEG 6 caprylic/ capric glycerides and PEG 75 soy glycerides. Also useful are C8–C12 acyl lactylates such as sodium lauroyl lactylate sold as Pationic 138 C.(R). available from the Patterson Chemical Company. Amounts of these agents may range from about 0.1 to 2%, preferably from about 0.5 to 1% by weight.

Cationic Polymers

Cationic polymers are also used in the inventive composition. Examples of the polymeric type include: cationic cellulose derivatives, cationic starches, copolymers of a diallyl quaternary ammonium salt and an acryl amide, quaternized vinylpyrrolidone vinylimidazole polymers polyglycol amine condensates, quaternized collagen polypeptide, polyethylene imine, cationized silicon polymer (e.g. Amodimethicone), cationic silicon polymers provided in a mixture with other components under the trademark Dow Corning 929 (cationized emulsion), copolymers of adipic acid and dimethylaminohydroxypropyl diethylenetriamine, cationic chitin derivatives, cationized guar gum (e.g. Jaguar C-B-S, Jaguar C-17, Jaguar C-16, etc. manufactured by the Celanese Company), quaternary ammonium salt polymers (e.g. Mirapol A-15, Mirapol AD-1, Mirapol AZ-1, etc., manufactured by the Miranol Divison of the Rhone Poulenc Company). Most preferred is polyquaternium-10 available as Polymer JR400 sold by the Amerchol Corporation.

Amounts of the cationic polymer may range from about 0.01 to 3.0%, preferably from about 0.01 to 1.0%, and most preferably from about 0.01 to 0.5% by weight.

In a preferred embodiment, the compositions of this invention are transparent. By the term transparent is meant having a maximum transmittance of light of at least 4% of any wave length in the range of 400 to 700 nm through a sample 1 cm thick. A transparent composition is one which also permits sufficient light transmittance to enable reading of newspaper print through a thickness commensurate with a diameter of the container employed with the herein described dispenser.

Antimicrobial Actives

Examples of suitable antibacterial agents which can be used herein include, but are not limited to, the dicarbanilides, for example, triclocarban also known as trchlorocarbanilide, triclosan, hexachlorophene and 3,4,5-tribromosalicylanilide, and the like. A preferred antibacterial agent herein is triclosan. Other suitable antibacterial actives include pharmaceutically-acceptable salts of b-lactam drugs, quinolone drugs, ciprofloxacin, norfloxacin, tetracycline, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole and amanfadine and mixtures thereof, and the like.

Non-aerosol Foaming Dispenser

An element of the cleansing product according to this invention is a non-aerosol foaming dispenser. A suitable dispenser may be mechanical and is generally characterized by a container for storing the composition (preferably a transparent container), a dispensing head defined by a housing containing a pump, and a dip tube for transferring the composition from the container into the dispensing head. Foam is created by requiring the composition to pass through a screen material which may be a porous substance such as a sintered material, a wire (plastic or metal) gauze screen or similar structures.

Suitable mechanical dispensers are described in U.S. Pat. No. 3,709,437 (Wright), U.S. Pat. No. 3,937,364 (Wright), U.S. Pat. No. 4,022,351 (Wright), U.S. Pat. No. 4,147,306 (Bennett), U.S. Pat. No. 4,184,615 (Wright), U.S. Pat. No. 4,598,862 (Rice), U.S. Pat. No. 4,615,467 (Grogan et al.) and U.S. Pat. No. 5,364,031 (Tamiguchi et al.). Most preferred however is a device owned by the Airspray International Corporation described in WO 97/13585 (Van der Heijden). All these patents are incorporated herein by reference. The Airspray device comprises a container for storing a cleansing composition and a dispensing head, the latter including at least a concentric air pump and liquid pump. Each of the pumps has a piston chamber with a piston displaceable therein and an inlet and discharge, and an operating component for operating the two pumps. The operating component is integral with one of the pistons and comprises an outflow channel with a dispensing opening. Shut-off mechanisms, rendering it possible to suck up air or liquid, respectively, and dispense them, are present in the inlet and discharge of the pumps. The air pump includes a double-acting shut-off device which can be operated actively by the operating component. The shut-off device prevents both the inlet of air to the air pump and discharge of air therefrom. The air piston is able to be moved freely at least over a small distance with respect to the operating component.

Other suitable foaming dispensers may include squeeze foamers. Squeeze foamer packages are well known as exemplified by the disclosures in the following patents that are incorporated herein by reference. U.S. Pat. No. 3,709,437, Wright, issued Jan. 9, 1973; U.S. Pat. No. 3,937,364, Wright, issued Feb. 10, 1976; U.S. Pat. No. 4,022,351, Wright, issued May 10, 1977; U.S. Pat. No. 4,147,306, Bennett, issued Apr. 3, 1979; U.S. Pat. No. 4,184,615, Wright, issued Jan. 22, 1980; U.S. Pat. No. 4,598,862, Rice, issued Jul. 8, 1986; and U.S. Pat. No. 4,615,467, Grogan et al., issued Oct. 7, 1986; and French Pat. 2,604,622, Verhulst, published Apr. 8, 1988.

When squeeze foamers are used, the composition is placed in the container reservoir (plastic squeeze bottle). Squeezing the container with the hand forces the composition through a foamer head, or other foam producing means, where the composition is mixed with air and then through a homogenizing means that makes the foam more homogeneous and controls the consistency of the foam. The foam is then discharged as a uniform, non-pressurized aerated foam.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLE 1

Solutions 1 to 5 represent embodiments of the inventive composition

TABLE 1

| INCI Ingredient | % active in formula | | | | |
|---|---|---|---|---|---|
| | Solution 1 | Solution 2 | Solution 3 | Solution 4 | Solution 5 |
| Water | q.s. 100 | q.s. 100 | q.s. 100 | q.s. 100 | q.s. 101 |
| tetrasodium EDTA | 0.078% | 0.078% | 0.078% | 0.078% | 0.078% |
| SLS | 4.600% | | | | |
| SLES, 2 EO | 3.80% | 5.00% | 4.00% | 5.60% | 5.00% |
| Cocoamidopropyl Betaine | | 2.50% | 2.52% | 1.00% | 1.00% |
| Alpha olefin sulfonate | | | 2.43% | | |
| Decyl Glucoside | | | | | 1.00% |
| Cocamide MEA | 1.20% | 0.40% | | | |
| Sodium Lauroamphoacetate | | | | 0.50% | |
| Sodium Lauroyl lactylate | | | | 0.20% | |
| Polyquaternium-10 | 0.13% | 0.07% | 0.05% | 0.05% | 0.07% |
| Wheatgermamidopropyl Hydroxypropyl Dimonium Hydrolyzed Wheat Protein | | 0.05% | | | 0.05% |
| PEG-400 | | 0.50% | | | |
| PEG 75 Soy Glycerides | | | | 0.20% | |
| Glycerin | 1.00% | 1.00% | | 1.00% | 1.00% |
| PEG-6 Caprylic/ Capric Glycerides | | 0.70% | | | 0.50% |
| DMDM Hydantoin | 0.20% | 0.20% | 0.20% | 0.20% | 0.20% |
| Citric Acid for pH adjustment | q.s. pH 4.5 | q.s. pH 4 | q.s. pH 4 | q.s. pH 5.5 | q.s. pH 4 |
| Fragrance | 0.50% | 0.50% | 0.50% | 0.50% | 0.50% |
| Triclosan | 0.15% | 0.15% | 0.15% | 0.15% | 0.15% |
| Lactic Acid | | | 2.00% | | |
| sodium hydroxide | | | 0.80% | | |
| pH | 4.5 | 4 | 4 | 5.5 | 4 |

EXAMPLE 2

The following procedure for antibacterial deposition testing was used to evaluate foam vs. liquid performance with regard to skin deposition.
Procedure for Deposition Testing
Pre Wash:
Wet forearms. Rub Dove bar in wet hands for 10 rotations of bar.
Wash both forearms for 30 seconds. Rinse for 15 seconds. Wait 30 minutes and take first extraction.
Extraction Procedure:
Place 1 inch glass cup on forearm.
Dispense 3 ml of Isopropanol into cup.
Scrub with glass stir rod for 30 seconds.
Draw off liquid and place in a glass vial.
Wash procedure:
For foam: Take 1 pump (Airspray International Co.) of foam product (solution 1 described in table 1). Rub for 30 seconds on forearm. Rinse for 10 seconds. Pat dry.
For liquid: Take 1 mL of neat liquid (not dispensed through Airspray pump). Rub for 30 seconds on other forearm. Rinse for 10 seconds. Pat dry.
Take the second extraction.
Pre and post extractions are measured for triclosan content.
Results:

TABLE 2

| Subject # | Triclosan deposited, $\mu g/cm^2$ | |
|---|---|---|
| | Foam Inventive | Liquid Comparative |
| 1 | 0.08364 | 0.05450 |
| 2 | 0.13093 | 0.07452 |

TABLE 2-continued

| Subject # | Triclosan deposited, $\mu g/cm^2$ | |
|---|---|---|
| | Foam Inventive | Liquid Comparative |
| 3 | 0.08119 | 0.06389 |
| 4 | 0.11169 | 0.21042 |

Results: 3 out of 4 panelists had significantly more triclosan deposited from the foam.

EXAMPLE 3

Solution 1 (as described in table 1) foamed (through the Airspray pump) and liquid (not dispensed through Airspray pump) was evaluated for waxy makeup removal.
Makeup Removal Protocol
1) Mark off two 3.5×2.5 cm rectangles on the inner side of each forearm.
2) Take skin color measurements using the Minolta Chromameter, 3 readings within each rectangle
3) Apply makeup as given below per type (all Revlon Colorstay):
Mascara—spread uniformly using spatula for even coverage allow 10 minutes for drying
4) Take color measurements on the dried makeup.
5) Wash with test product, as follows:
Wet arms.
Apply 1 ml of liquid or foam to the makeup site.
Rub product on site for 30 seconds
Rinse soap off for 15 seconds
6) Take skin color measurements on cleaned skin
7) Calculate the % makeup removed

TABLE 3

| Liquid (Comparative) | | Foam (Inventive) | |
|---|---|---|---|
| Percent removal | Std. Deviation (n = 15) | Percent removal | Std. Deviation (n = 15) |
| 68.43 | 23.00 | 81.30 | 20.00 |

The foregoing description and examples illustrate selected embodiments of the present invention. In light thereof variations and modifications will be suggested to one skilled in the art, all of which are within the scope and spirit of this invention.

We claim:

1. A foam producing, cleansing product comprising:
   (a) A foamable cleansing liquid composition including from about 0.1 to about 12 wt. % of a surfactant blend selected from anionic surfactants, amphoteric surfactants, nonionic surfactants, and mixtures thereof; said surfactant blend having at least one anionic surfactant: and at least one surfactant selected from an amphoteric and nonionic surfactant; wherein the sum of nonionic and amphoteric surfactants is in the range of about 0.5 to 12 wt. %;
   from about 0.01 to 3.0 wt. % of a water soluble cationic polymer;
   from about 0.05 to 1.5 wt. % of a hydrophobic antibacterial compound;
   (b) a mechanical foam dispenser for dispensing a foam from said liquid composition, said dispenser including a reservoir to contain said liquid composition, a manually actuated mechanism for generating a volume of foam, and a foam dispensing nozzle attached in fluid communication with said manually actuated mechanism; and
   (c) wherein said liquid composition contains less than about 0.05 wt. % of a water insoluble emollient.

2. The foam producing, cleansing product of claim 1 wherein the foam produced has a foam density of about 0.05 to 0.20 g/ml when dispensed from said foam dispenser.

3. The foam producing, cleansing product of claim 1 wherein the weight ratio of said anionic surfactant to the sum of said nonionic and amphoteric surfactants is in the range of 0.2 to 1 to 3 to 1.

4. The foam producing, cleansing product of claim 1 wherein the total amount of surfactants does not exceed about 10.5 wt. %.

5. The foam producing, cleansing product of claim 1 wherein the viscosity of said liquid composition is in the range of about 1 to 500 cps at 25 C.

6. The foam producing, cleansing product of claim 1 wherein the viscosity of said liquid composition is in the range of about 1 to 200 cps at 25 C.

7. The foam producing, cleansing product of claim 1 further comprising from about 0.5 to 10.0 wt. % of a water soluble emollient.

8. The foam producing, cleansing product of claim 1 wherein the antibacterial agent is selected from triclosan, trichlocarban, and chlorhexidine.

9. The foam producing, cleansing product of claim 1 wherein said liquid composition has a pH in the range of about 3.5 to 6.5.

10. The foam producing, cleansing product of claim 1 wherein said liquid composition has a pH in the range of about 4.0 to 5.5.

11. The foam producing, cleansing product of claim 1 wherein said liquid composition is clear.

12. A method of depositing a hydrophobic antibacterial agent onto the skin comprising the steps of:
    dispensing the foam producing, cleansing product of claim 1 onto the skin as a foam;
    rubbing said foam on the skin; and
    rinsing the excess foam from the skin with water.

13. The method of claim 12 wherein said foam has a foam density of about 0.05 to 0.20 g/ml when dispensed.

14. A method of removing waxy cosmetics from the skin comprising the steps of:
    dispensing the foam producing, cleansing product of claim 1 onto the skin as a foam;
    rubbing said product on the skin coated with said waxy cosmetics; and
    rinsing the thus loosened cosmetics and excess product from the skin with water.

15. The method of claim 14 wherein said foam has a foam density of about 0.05 to 0.20 g/ml when dispensed.

* * * * *